(12) United States Patent
Orr (10) Patent No.: US 10,561,339 B2
(45) Date of Patent: Feb. 18, 2020

(54) SYSTEM AND METHOD FOR DETERMINING CARBON DIOXIDE EXCRETED DURING NON-INVASIVE VENTILATION

(75) Inventor: Joseph Allen Orr, Park City, UT (US)

(73) Assignee: Koninklijke Philips N.V., Eindhoven (NL)

(*) Notice: Subject to any disclaimer, the term of this patent is extended or adjusted under 35 U.S.C. 154(b) by 688 days.

(21) Appl. No.: 13/994,545

(22) PCT Filed: Dec. 13, 2011

(86) PCT No.: PCT/IB2011/055625
§ 371 (c)(1),
(2), (4) Date: Jun. 14, 2013

(87) PCT Pub. No.: WO2012/085753
PCT Pub. Date: Jun. 28, 2012

(65) Prior Publication Data
US 2013/0267863 A1 Oct. 10, 2013

Related U.S. Application Data

(60) Provisional application No. 61/555,911, filed on Nov. 4, 2011, provisional application No. 61/425,559, filed on Dec. 21, 2010.

(51) Int. Cl.
*A61B 5/08* (2006.01)
*A61B 5/087* (2006.01)
(Continued)

(52) U.S. Cl.
CPC .............. *A61B 5/082* (2013.01); *A61B 5/087* (2013.01); *A61B 5/4836* (2013.01); *A61B 5/72* (2013.01);
(Continued)

(58) Field of Classification Search
None
See application file for complete search history.

(56) References Cited

U.S. PATENT DOCUMENTS

| 5,495,744 A | 3/1996 | Ueda et al. |
| 6,059,732 A * | 5/2000 | Orr ................ A61B 5/083 600/531 |

(Continued)

FOREIGN PATENT DOCUMENTS

| DE | 102007054390 A1 | 5/2008 |
| JP | H08243165 A | 9/1996 |

(Continued)

OTHER PUBLICATIONS

Kline, Jeffrey A., et al. "Diagnostic accuracy of a bedside D-dimer assay and alveolar dead-space measurement for rapid exclusion of pulmonary embolism: a multicenter study." Jama 285.6 (2001): 761-768.*

*Primary Examiner* — Daniel L Cerioni
*Assistant Examiner* — Jairo H Portillo
(74) *Attorney, Agent, or Firm* — Michael W. Haas (57) ABSTRACT

A system is configured to perform capnometry/capnography, and/or other compositional analysis on a non-invasively ventilated subject. As such, the system determines amounts of a molecular species of gas (e.g., carbon dioxide, oxygen, etc.) excreted by the subject on a per-breath basis. Determinations of amounts of the molecular species of gas excreted are adjusted to reflect amounts of the molecular species of gas leaked from the non-invasive interface used to communicate with the airway of the subject.

18 Claims, 3 Drawing Sheets

(51) Int. Cl.
*A61B 5/00* (2006.01)
*A61M 16/00* (2006.01)
*A61M 16/04* (2006.01)
*A61M 16/06* (2006.01)
*A61M 16/08* (2006.01)
*A61M 16/20* (2006.01)

(52) U.S. Cl.
CPC .... *A61M 16/0066* (2013.01); *A61M 16/0434* (2013.01); *A61M 16/0666* (2013.01); *A61M 16/0875* (2013.01); *A61M 16/20* (2013.01)

(56) References Cited

U.S. PATENT DOCUMENTS

| | | | |
|---|---|---|---|
| 6,152,129 A * | 11/2000 | Berthon-Jones | A61M 16/0057 128/200.24 |
| 6,599,252 B2 * | 7/2003 | Starr | A61B 5/091 600/532 |
| 7,556,039 B1 * | 7/2009 | Pierry | A61B 5/0836 128/204.18 |
| 7,810,497 B2 | 10/2010 | Pittman et al. | |
| 8,272,380 B2 | 9/2012 | Jafari | |
| 2002/0138213 A1 | 9/2002 | Mault | |
| 2003/0065274 A1 * | 4/2003 | Mault | A61B 5/0833 600/531 |
| 2005/0177056 A1 * | 8/2005 | Giron | A61M 16/0666 600/543 |
| 2006/0111749 A1 * | 5/2006 | Westenskow | A61M 16/00 607/5 |
| 2007/0144522 A1 * | 6/2007 | Eger | A61M 16/0051 128/205.23 |
| 2007/0221224 A1 | 9/2007 | Pittman | |
| 2008/0072905 A1 * | 3/2008 | Baker | A61B 5/0836 128/204.23 |
| 2010/0101577 A1 * | 4/2010 | Kaestle | A61B 5/0833 128/204.22 |
| 2011/0245705 A1 | 10/2011 | Orr et al. | |
| 2013/0267863 A1 | 10/2013 | Orr | |

FOREIGN PATENT DOCUMENTS

| | | |
|---|---|---|
| WO | 03105720 A2 | 12/2003 |
| WO | 2003105720 A2 | 12/2003 |

* cited by examiner

SYSTEM AND METHOD FOR DETERMINING CARBON DIOXIDE EXCRETED DURING NON-INVASIVE VENTILATION

BACKGROUND

1. Field of the Disclosure

The invention relates to determining the amount of carbon dioxide, and/or some other molecular species of gas, excreted during non-invasive ventilation.

2. Description of the Related Art

During invasive ventilation a sealed engagement is maintained between a respiratory circuit and the airway of the subject by an invasive interface appliance. For example, an endotracheal tube may maintain such a seal as pressurized gas is delivered to mechanically ventilate the subject. In such a configuration, determining excreted carbon dioxide or some other molecular species (e.g., to monitor gas exchange) may be fairly straightforward.

In non-invasive ventilation, pressurized gas causing mechanical ventilation is delivered to the airway of a subject via a non-invasive interface appliance. The non-invasive interface appliance interfaces in an unsealed manner with one or more external orifices of the airway of the subject. For example, a breathing mask forms a cavity that engages the face of the subject about the nose and mouth. Because non-invasive interface appliances allow for leakage of gas during respiration, accurate and/or precise detection of carbon dioxide may be more complicated (e.g., as excreted gas escapes through leaks).

SUMMARY

One aspect of the disclosure relates to a system configured to determine a volume of carbon dioxide excreted by a subject during respiration. In one embodiment, the system comprises one or more gas parameter sensors, a carbon dioxide sensor, and a processor. The one or more gas parameter sensors are configured to generate output signals conveying information related to pressure and/or flow in a respiratory circuit. The respiratory circuit comprises a non-invasive subject interface appliance configured to non-invasively communicate with the airway of a subject. The carbon dioxide sensor is configured to generate output signals conveying information related to the concentration of carbon dioxide present in the respiratory circuit. The processor is configured to execute one or more modules including a concentration module, a leak module, and a carbon dioxide module. The concentration module is configured to determine the concentration of carbon dioxide in gas expired from the airway of the subject during expiration based on the output signals generated by the carbon dioxide sensor. The leak module is configured to estimate gas leakage from the respiratory circuit during respiration based on the output signals generated by the one or more gas parameters sensors. The carbon dioxide volume module is configured to determine volumes of carbon dioxide excreted by the subject during individual breaths based on (i) the determination of the concentration of carbon dioxide by the concentration module, (ii) the estimate of gas leakage from the respiratory circuit by the leak module, and (iii) the output signals generated by the one or more gas parameters sensors and the carbon dioxide sensor, wherein the carbon dioxide volume module is configured such that the determination of the volume of carbon dioxide excreted during a given breath is adjusted to include an estimate of the carbon dioxide leaked during expiration and an estimate of the carbon dioxide leaked during inspiration.

Another aspect of the disclosure relates to a method of determining a volume of carbon dioxide excreted by a subject during respiration. In one embodiment, the method comprises generating output signals conveying information related to pressure and/or flow in a respiratory circuit, wherein the respiratory circuit comprises a non-invasive subject interface appliance configured to non-invasively communicate with the airway of a subject; generating output signals conveying information related to the concentration of carbon dioxide present in the respiratory circuit; determining the concentration of carbon dioxide in gas expired from the airway of the subject during expiration based on the output signals conveying information related to the concentration of carbon dioxide present in the respiratory circuit; estimating gas leakage from the respiratory circuit during respiration based on the output signals conveying information related to pressure and/or flow in the respiratory circuit; and determining volumes of carbon dioxide excreted by the subject during individual breaths based on (i) the determination of the concentration of carbon dioxide in gas expired from the airway of the subject, (ii) the estimate of gas leakage from the respiratory circuit, and (iii) the generated output signals, wherein determination of the volume of carbon dioxide excreted during a given breath is adjusted to include an estimate of the carbon dioxide leaked during expiration and an estimate of the carbon dioxide leaked during inspiration.

Yet another aspect of the invention relates to a system for determining a volume of carbon dioxide excreted by a subject during respiration. In one embodiment, the system comprises means for generating output signals conveying information related to pressure and/or flow in a respiratory circuit, wherein the respiratory circuit comprises a non-invasive subject interface appliance configured to non-invasively communicate with the airway of a subject; means for generating generate output signals conveying information related to the concentration of carbon dioxide present in the respiratory circuit; means for determining the concentration of carbon dioxide in gas expired from the airway of the subject during expiration based on the output signals conveying information related to the concentration of carbon dioxide present in the respiratory circuit; means for estimating gas leakage from the respiratory circuit during respiration based on the output signals conveying information related to pressure and/or flow in the respiratory circuit; and means for determining volumes of carbon dioxide excreted by the subject during individual breaths based on (i) the determination of the concentration of carbon dioxide in gas expired from the airway of the subject, (ii) the estimate of gas leakage from the respiratory circuit, and (iii) the generated output signals, wherein determination of the volume of carbon dioxide excreted during a given breath is adjusted to include an estimate of the carbon dioxide leaked during expiration and an estimate of the carbon dioxide leaked during inspiration.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
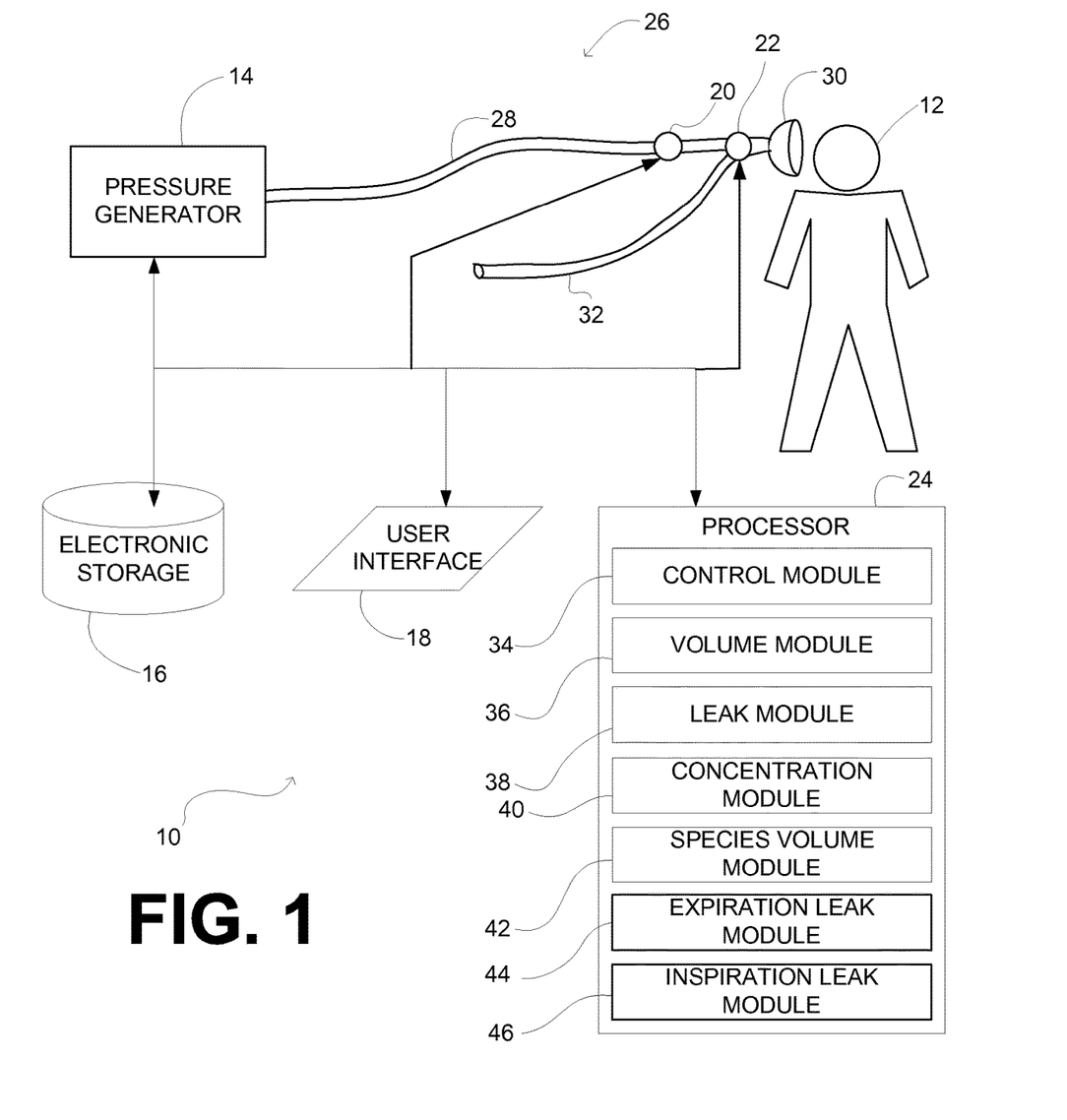
FIG. 1 illustrates a system configured to determine the volume of a molecular species of gas excreted by a subject during respiration.

FIG. 1 illustrates a system 10 configured to perform capnometry/capnography, and/or other compositional analysis on a non-invasively ventilated subject 12. As such, system 10 determines amounts of a molecular species of gas (e.g., carbon dioxide, oxygen, etc.) excreted by subject 12 on a per-breath basis. Determinations of amounts of the molecular species of gas excreted are adjusted to reflect amounts of the molecular species of gas leaked from the non-invasive interface used to communicate with the airway of subject 12. In one embodiment, system 10 includes one or more of a pressure generator 14, electronic storage 16, a user interface 18, one or more gas parameter sensors 20, a concentration sensor 22, a processor 24, and/or other components.

In one embodiment, pressure generator 14 is configured to generate a pressurized flow of breathable gas for delivery to the airway of subject 12. The pressure generator 14 may control one or more parameters of the pressurized flow of breathable gas (e.g., flow rate, pressure, volume, humidity, temperature, gas composition, etc.) for therapeutic purposes, or for other purposes. By way of non-limiting example, pressure generator 14 may be configured to control the pressure of the pressurized flow of breathable gas to provide mechanical ventilation to the subject 12 (e.g., raise and lower pressure at the airway of subject 12 to cause gas exchange with the lungs of subject 12). The pressure generator 14 may include a blower, a bellows, a wall gas source, a pressurized body of gas (e.g., in a canister), and/or other sources of pressurization.

The pressurized flow of breathable gas is delivered to the airway of subject 12 via a subject interface 26. Subject interface 26 is configured to communicate the pressurized flow of breathable gas generated by pressure generator 14 to the airway of subject 12. As such, subject interface 26 includes a conduit 28 and an interface appliance 30. Conduit 28 conveys the pressurized flow of breathable gas to interface appliance 30, and interface appliance 30 delivers the pressurized flow of breathable gas to the airway of subject 12. The subject interface 26 is non-invasive. As such, interface appliance 30 non-invasive engages subject 12 to deliver the pressurized flow of breathable gas. Non-invasive engagement includes removably engaging an area (or areas) surrounding one or more external orifices of the airway of subject 12 (e.g., nostrils and/or mouth) to communicate gas between the airway of subject 12 and subject interface 26. Some examples of non-invasive interface appliance 30 may include, for example, a nasal cannula, a nasal mask, a nasal/oral mask, a full face mask, a total face mask, or other interface appliances that communicate a flow of gas with an airway of a subject. Examples of an invasive interface appliance, which would not serve as interface appliance 30 in subject interface 26, include an endotracheal tube, laryngeal mask airway, and/or other invasive interface appliances.

To facilitate expiration by subject 12, subject interface 26 further includes an exhaust conduit 32. The exhaust conduit 32 is configured to receive gas expired from the lungs of subject 12, and to exhaust the expired gas (e.g., to atmosphere, through a filter, etc.). In one embodiment, a valve (not shown) selectively opens and closes exhaust conduit 32 in time with the mechanical respiration provided by system 10. This includes opening the valve to exhaust expired gas during expiration and closing the valve to slow or cease exhaustion of gas during inspiration.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., generator 14, user interface 18, processor 24, etc.).

User interface 18 is configured to provide an interface between system 10 and one or more users (e.g., subject 12, a caregiver, a researcher, a therapy decision-maker, etc.) through which the users may provide information to and receive information from system 10. This enables data, cues, results, and/or instructions and any other communicable items, collectively referred to as "information," to be communicated between the users and one or more of pressure generator 14, electronic storage 16, and/or processor 24. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with generator 14.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

The gas parameter sensors 20 are configured to generate output signals conveying information related to one or more gas parameters of the gas within subject interface 26. The one or more gas parameters may include, for example, flow, volume, pressure, and/or other gas parameters. The gas parameter sensors 20 may include one or more sensors that measure such parameters directly (e.g., through fluid communication with the pressurized flow of breathable gas at pressure generator 14 or in subject interface 26). The gas parameter sensors 20 may include one or more sensors that generate output signals related to one or more parameters of the pressurized flow of breathable gas indirectly. For example, one or more of sensors 20 may generate an output based on an operating parameter of pressure generator 14 (e.g., a valve driver or motor current, voltage, rotational velocity, and/or other operating parameters), and/or other sensors. Although gas parameter sensors 20 are illustrated at a single location at or adjacent to an interface between interface appliance 30 and conduits 26 and 28, this is not intended to be limiting. The gas parameter sensors 20 may include sensors disposed in a plurality of locations, such as for example, within pressure generator 14, within (or in communication with) conduit 28, within (or in communication with) interface appliance 30, within exhaust conduit 32, and/or other locations.

The concentration sensor 22 is configured to generate output signals conveying information related to a concentration of a molecular species of gas in the gas within subject interface 26. The molecular species of gas may be carbon dioxide, oxygen, and/or other molecular species. The description herein of the molecular species of gas as being carbon dioxide is not intended to be limiting. In the embodiment of system 10 illustrated in FIG. 1, concentration sensor 22 is depicted as being located at an interface between interface appliance 30 and conduits 28 and 32. This is not intended to be limiting. The concentration sensor 22 may be disposed at other locations in system 10. For example, concentration sensor 22 may be disposed inline with exhaust conduit 32.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination. For example, processor 24 may represent a first processor (or processors) within a ventilator including pressure generator 14 and a second processor within a gas analysis device or system that is separate from the ventilator.

As is shown in FIG. 1, processor 24 may be configured to execute one or more computer program modules. The one or more computer program modules may include one or more of a control module 34, a volume module 36, a leak module 38, a concentration module 40, a species volume module 42, an expiration leak module 44, an inspiration leak module 46, and/or other modules. Processor 24 may be configured to execute modules 34, 36, 38, 40, 42, 44, and/or 46 by software; hardware; firmware; some combination of software, hardware, and/or firmware; and/or other mechanisms for configuring processing capabilities on processor 24.

It should be appreciated that although modules 34, 36, 38, 40, 42, 44, and 46 are illustrated in FIG. 1 as being co-located within a single processing unit, in implementations in which processor 24 includes multiple processing units, one or more of modules 34, 36, 38, 40, 42, 44, and/or 46 may be located remotely from the other modules. The description of the functionality provided by the different modules 34, 36, 38, 40, 42, 44, and/or 46 described below is for illustrative purposes, and is not intended to be limiting, as any of modules 34, 36, 38, 40, 42, 44, 46, and/or 46 may provide more or less functionality than is described. For example, one or more of modules 34, 36, 38, 40, 42, 44, and/or 46 may be eliminated, and some or all of its functionality may be provided by other ones of modules 34, 36, 38, 40, 42, 44, and/or 46. As another example, processor 24 may be configured to execute one or more additional modules that may perform some or all of the functionality attributed below to one of modules 34, 36, 38, 40, 42, 44, and/or 46.

The control module 34 is configured to control pressure generator 14 and/or the valve (not shown) controlling flow into exhaust conduit 32 in order to mechanically ventilate subject 12. The control module 34 is configured such that the pressurized flow of breathable gas generated by pressure generator 14 is provided to subject 12 in accordance with a therapy regimen that manually affects gas exchange with the lungs of subject 12. This include elevating pressure within subject interface 26 to a relatively high level to cause and/or promote inspiration, and reducing pressure within subject interface 26 to cause and/or promote expiration.

The volume module 36 is configured to determine volumetric measurements with respect to gas that is provided to and/or received from interface appliance 30. Such volumetric measurements include volume provided to interface appliance 30 during a breath ($V_{in}$), and volume received from interface appliance 30 (e.g., into exhaust conduit 32) during a breath ($T_{out}$). The volume module 36 is configured to determine these measurements based on the output signals generated by gas parameter sensors 20 and/or other information. The volume module 36 is further configured to determine the tidal volume of inspiration ($VT_{insp}$) and the tidal volume of expiration ($VT_{exp}$). The tidal volume of inspiration and the tidal volume of expiration can be determined according to the following relationship:)

$$VT_{insp}=V_{in}-V_{insp\_leak}; \text{ and} \quad (1)$$

$$VT_{exp}=V_{out}+V_{exp\_leak}; \quad (2)$$

wherein $V_{insp\_leak}$ represents the volume of gas leaked through subject interface 26 and/or the engagement between interface appliance 30 and subject 12 during inspiration, and $V_{exp\_leak}$ represents the volume of gas leaked through subject interface 26 and/or the engagement between interface appliance 30 and subject 12 during expiration. As is discussed herein, the volume of leak during inspiration and the volume of leak during expiration are determined by leak module 38.

The leak module 38 is configured to estimate gas leakage from subject interface 26 during respiration. The gas leakage from subject interface 26 includes gas leaked from subject interface 26 and/or the interface between subject 12 and interface appliance 30. The leak module 38 is configured to estimate gas leakage as a function of pressure in subject interface 26 (or as a function of the output signals of gas parameter sensors 20 conveying information about pressure). In one embodiment, leakage is estimated in accordance with one of the following relationships:

$$L=K*P; \text{ or} \tag{3}$$

$$L=K*\sqrt{P}; \tag{4}$$

where L represents the rate of leakage, K represents a proportionality metric, and P represents pressure in subject interface 26. From the rate of leakage during inspiration and the rate of leakage during expiration, leak module 38 determines the volume of leak during inspiration ($V_{insp\_leak}$) and the volume of leak during expiration ($V_{exp\_leak}$). $V_{insp\_leak}$ is the sum (integral) of the leak L during the inspiratory period of the breath and $V_{exp\_leak}$ is the sum (integral) of the leak flow (L) during the expiratory phase of the breath.

The leak module 38 is further configured to determine K. The determination of K may be dynamic and ongoing. In one embodiment, leak module 38 determines K for a given breath n ($K_n$) as follows:

$$K_n=K_{n-1}+\alpha*(VT_{insp}-VT_{exp}); \tag{5}$$

where $K_{n-1}$ represents K of the breath prior to breath n, and α represents small constant (e.g., about 0.2), which may be predetermined. In one embodiment, the tidal volume difference ($VT_{insp}-VT_{exp}$) is lowpass filtered to remove breath-to-breath volume differences. It will be appreciated that this particular technique for determining the proportionality metric K is not intended to be limiting, and the scope of this disclosure includes other techniques for determining this metric.

The concentration module 40 is configured to determine the concentration of a molecular species of gas, such as carbon dioxide, in gas expired by subject 12. The concentration is determined based on the output signals generated by concentration sensor 22. The concentration module may be configured to adjust a concentration measured by concentration sensor 22 to account for a volume of subject interface 26 between concentration sensor 22 and the airway of subject 12. The volume of subject interface 26 between concentration sensor 22 and the airway of subject 12 is referred to herein as the "mask volume" even though this volume may include more or less volume than the volume of interface appliance 30.

If we assume that the mask volume is completely mixed, then for the end-tidal carbon dioxide concentration as measured at concentration sensor 22 to be within 5% of the actual (mouth) end-tidal carbon dioxide concentration, then the alveolar expired tidal volume must be at least three times the mask volume. In other words, if the expired volume is not sufficient to mix out the inspired gas stored upstream from concentration sensor 22 at the end of inspiration, then the end-tidal carbon dioxide concentration as measured by concentration sensor 22 will not be indicative of the CO2 concentration of the gas at the airway of subject 12, and/or the of the gas that leaks from subject interface 26. The ratio of mask volume to tidal volume is analogous to the ratio of a time constant to decay time. If a tidal volume passing through subject interface 26 is exactly equal to the mask volume, then the measured end-tidal carbon dioxide concentration measured at concentration sensor 22 will be 63% of the true end-tidal carbon dioxide concentration. A tidal volume equal to two mask volumes gives a measured end-tidal carbon dioxide concentration that is 86.4% of the true value and so on. Accordingly, the end-tidal carbon dioxide concentration at the airway of subject 12 can be determined as follows:

$$F_{CO2sensor}=F_{CO2mouth}*(1-e^{-[VTexp\_period/Vmask]}); \tag{6}$$

where $F_{CO2sensor}$ represents the measured concentration at concentration sensor 22, $F_{CO2mouth}$ represents the concentration at the airway of subject 12, $V_{mask}$ represents the mask volume, and $VT_{exp\_period}$ is the volume of expired air that the subject 12 exhales into the mask before the time when the flow of gas as seen at the sensor reverses. This is calculated as the sum (integral) of $flow_{sensor}+flow_{exp\_leak}$ during the period between the beginning of expiration and the time that gas flow as measured by the sensor 20 transitions from negative to positive flow. $Flow_{sensor}$ is the flow as measured by the sensor during expiration and $flow_{exp\_leak}$ is the leak (L) as calculated in equation 3 or 4 during expiration. Even though the subject 12 may continue to exhale after this time, the added flow of gas from the ventilator into the mask changes the assumption that all gas added to the mask volume is from the subject 12. It will be appreciated that equation (6) models the mask volume as a first order mixing chamber. Other approximations and/or models for simulating the mixing of carbon dioxide within the mask volume may be implemented without departing from the scope of this disclosure. According to the relationship shown in equation (6), end-tidal carbon dioxide concentration at the airway can be determined from an end-tidal carbon dioxide concentration measured at concentration sensor 22 as follows:

$$etCO2_{mouth}=etCO2_{sensor}/(1-e^{-[VTexp\_period/Vmask]}); \tag{7}$$

where $etCO2_{mouth}$ represents end-tidal carbon dioxide concentration at the airway of subject 12, and $etCO2_{sensor}$ represents end-tidal carbon dioxide concentration at concentration sensor 22.

The species volume module 42 is configured to determine one or more volumes of the molecular species of gas, such as carbon dioxide. These volumes may include, for example, the volume of carbon dioxide inspired during a breath ($VCO2_{inspired}$), the volume of expired carbon dioxide ($VCO2_{expired}$), the volume of excreted carbon dioxide measured by concentration sensor 22 during a breath ($VCO2_{measured}$), the total volume of excreted carbon dioxide during a breath (VCO2), and/or other volumes.

The determination of carbon dioxide inspired during a breath may be determined according to the following relationship:

$$VCO2_{inspired}=V_{in}*FCO2_{sensor}; \tag{8}$$

The determination of the volume of carbon dioxide expired from interface appliance 30 via subject interface 26 during a breath may be determined according to the following relationship:

$$VCO2_{expired}=V_{out}*FCO2_{sensor}. \tag{9}$$

The determination of the volume of excreted carbon dioxide measured by concentration sensor 22 during a breath may be determined according to the following relationship:

$$VCO2_{measured}=VCO2_{expired}-VCO2_{inspired}. \tag{10}$$

The species volume module 42 is configured such that the determination of volume of carbon dioxide excreted by subject 12 during a breath (VCO2) includes an adjustment for carbon dioxide leaked during expiration, and/or an adjustment for carbon dioxide leaked during a subsequent inspiration. As such, species volume module 42 is configured to determine the volume of carbon dioxide excreted during a breath as the sum of the volume of excreted carbon dioxide measured at the concentration sensor 22 during expiration ($VCO2_{measured}$), the amount of carbon dioxide lost through leak during expiration ($VCO2_{exp\_leak}$), and/or the amount of carbon dioxide that was stored in the subject interface 26 that leaks out during the subsequent inspiration ($VCO2_{insp\_leak}$). This can be expressed as follows:

$$VCO2 = VCO2_{measured} + VCO2_{exp\_leak} + VCO2_{insp\_leak}. \quad (11)$$

The expiration leak module 44 is configured to estimate carbon dioxide leaked during expiration ($VCO2_{exp\_leak}$). This estimation may be implemented by species volume module 42 to adjust the determination of total carbon dioxide excreted during a breath (e.g., according to the relationship set forth in equation (11)). This estimation is based on the determination of carbon dioxide concentration by concentration module 40 ($etCO2_{sensor}$ and/or $etCO2_{mouth}$), estimates of gas leakage by leak module 38, the output signals generated by gas parameter sensors 20 and/or concentration sensor 22, and/or other information.

In one embodiment, the volume of carbon dioxide leaked during expiration ($VCO2_{exp\_leak}$), is assumed to be proportional to the total expired leak volume ($V_{exp\_leak}$ as determined by leak module 38) multiplied by the end-tidal carbon dioxide fraction as measured by the sensor 22. Because the fraction of carbon dioxide in the mask is not at the end-tidal concentration throughout the entire breath, the calculation must be adjusted to account for the residual gas in the mask at the start of expiration and the airway dead space gas in the trachea. After this gas has been cleared from the mask, the remainder is at the end-tidal carbon dioxide concentration. The volume of carbon dioxide that is leaked during expiration is therefore the volume of gas leaked ($VT_{exp\_leak}$) multiplied by the end-tidal carbon dioxide fraction as measured by the sensor 22. This amount is further reduced by the fraction of the expired gas ($VT_{exp}$) that is not dead volume (Vd) divided by the total expired tidal volume ($VT_{exp}$ as determined by volume module 36). The volume of exhaled carbon dioxide passes through the portion of subject interface 26 between the airway of subject 12 and concentration sensor 22 is the sum of the volume of carbon dioxide excreted per breath measured by concentration sensor 22 ($VCO2_{measured}$) and the measured inspired volume of carbon dioxide per breath ($VCO2_{inspired}$). The equation below gives the volume of carbon dioxide per breath that is lost due to leak during expiration:

$$VCO2_{exp\_leak} = etCO2_{sensor} * VT_{exp\_leak} * (VT_{exp} - V_d) / VT_{exp}; \quad (12)$$

where $VT_{exp\_leak}$ is the total volume that was leaked out of the mask during expiration, $VT_{exp}$ is the corrected expiratory tidal volume, $etCO2_{sensor}$ is the measured (non-compensated) end tidal carbon dioxide fraction for the current breath as measured by the sensor, and Vd is the airway dead space which is comprised of the mask volume and the anatomic dead space. Note that Vd is the total airway dead space which is the sum of the anatomic dead space (trachea, bronchioles, etc. and the dead space caused by the mask $V_{mask}$). Alternatively, if the volumetric average expired carbon dioxide fraction is used in place of end tidal carbon dioxide, then the subtraction of Vd in equation 12 is not necessary.

The inspiration leak module 46 is configured to estimate carbon dioxide leaked during inspiration ($VCO2_{insp\_leak}$). This estimation may be implemented by species volume module 42 to adjust the determination of total carbon dioxide excreted during a breath (e.g., according to the relationship set forth in equation (11)). This estimation is based on the determination of carbon dioxide concentration by concentration module 40 ($etCO2_{sensor}$ and/or $etCO2_{mouth}$), estimates of gas leakage by leak module 38, the output signals generated by gas parameter sensors 20 and/or concentration sensor 22, and/or other information.

The volume of carbon dioxide that escapes through leakage during inspiration is a fraction of the residual carbon dioxide left in subject interface 26 between concentration sensor 22 and the airway of subject 12. The fraction of the leaked carbon dioxide is assumed to be proportional to the ratio of leaked gas to total inspired tidal volume. This is represented in the following relationship:

$$VCO2_{insp\_leak} = (VT_{insp\_leak}/VT_{insp}) * (V_{mask} * etCO2_{mouth} + VCO2_{insp}); \quad (13)$$

where $VCO2_{insp\_leak}$ represents the volume of carbon dioxide that is left in the mask volume ($V_{mask}$) at the end of expiration and the volume of carbon dioxide that enters the mask from the pressure source during inspiration that is leaked rather than inhaled by the patient. $VT_{insp\_leak}$ is the volume of gas that is leaked during inspiration, $VT_{insp}$ is the inspiratory tidal volume, $V_{mask}$ is the mask volume and $etCO2_{mouth}$ is the end-tidal fraction of carbon dioxide at the mouth as calculated in equation 7 above.

Figure 2:
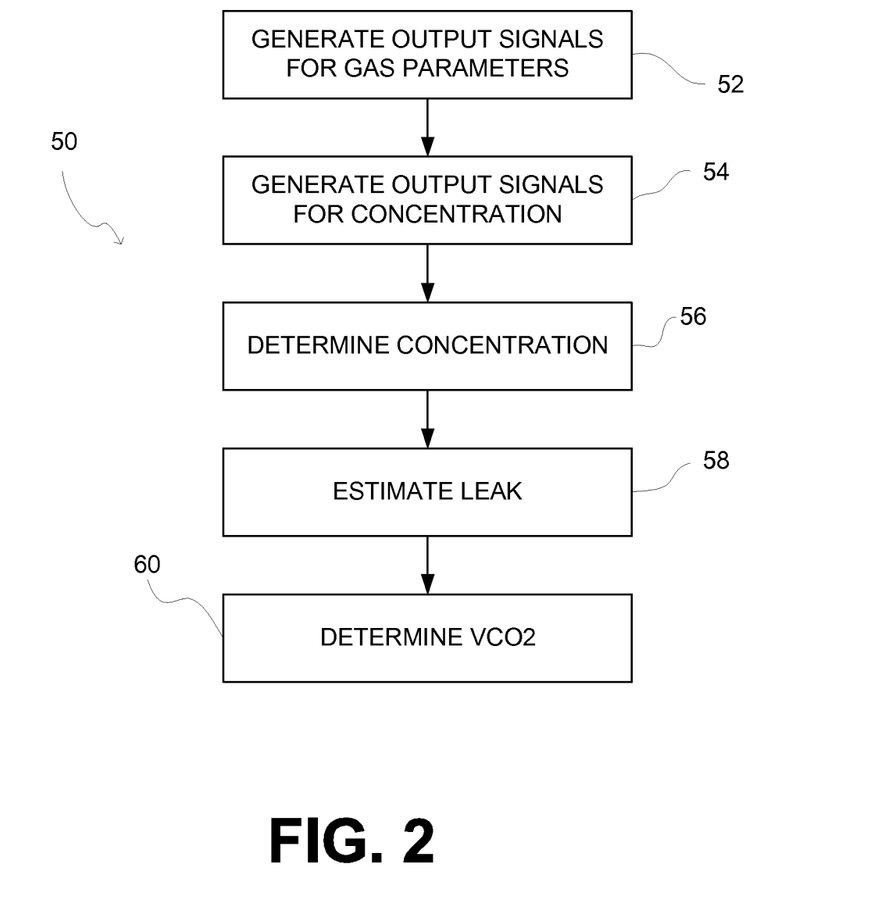
FIG. 2 illustrates a method of determining the volume of a molecular species of gas excreted by a subject during respiration.

FIG. 2 illustrates a method 50 of determining a volume of carbon dioxide excreted by a subject during respiration. The operations of method 50 presented below are intended to be illustrative. In some embodiments, method 50 may be accomplished with one or more additional operations not described, and/or without one or more of the operations discussed. Additionally, the order in which the operations of method 50 are illustrated in FIG. 2 and described below is not intended to be limiting.

In some embodiments, method 50 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 50 in response to instructions stored electronically on an electronic storage medium. The one or more processing devices may include one or more devices configured through hardware, firmware, and/or software to be specifically designed for execution of one or more of the operations of method 50.

At an operation 52, output signals conveying information related to pressure and/or flow in a respiratory circuit are generated. The respiratory circuit includes a non-invasive subject interface appliance. In one embodiment, the respiratory circuit is similar to or the same as subject interface 26 (shown in FIG. 1 and described above). In one embodiment, operation 52 is performed by one or more gas parameter sensors similar to or the same as gas parameter sensors 20 (shown in FIG. 1 and described above).

At an operation 54, output signals conveying information related to the concentration of a gaseous molecular species present in the respiratory circuit are generated. The gaseous molecular species may be carbon dioxide. In one embodiment, operation 54 is performed by a concentration sensor similar to or the same as concentration sensor 22 (shown in FIG. 1 and described above).

At an operation 56, the concentration of the gaseous molecular species present in the respiratory circuit is determined. The concentration determined may be the concentration at a concentration sensor, at the airway of the subject, and/or other concentrations. In one embodiment, operation 56 is performed by a concentration module similar to or the same as concentration module 40 (shown in FIG. 1 and described above).

At an operation 58, an amount of gas leaked from the respiratory circuit during respiration is estimated. The amount of gas leaked may be determined from the output signals generated at operation 52. In one embodiment, operation 58 is performed by a leak module similar to or the same as leak module 38 (shown in FIG. 1 and described above).

At an operation 60 a volume of the molecular species excreted by the subject during a breath is determined. The determination may be based on one or more of the determination of the concentration of carbon dioxide in gas expired from the airway of the subject made at operation 56, the estimate of gas leakage from the respiratory circuit made at operation 58, the output signals generated at operation 52 and/or 54, and/or other information. The determination made at operation 60 includes an adjustment for an estimate of the molecular species leaked during expiration, and/or for an estimate of the molecular species leaked during the subsequent inspiration. In one embodiment, operation 60 is performed by a species volume module similar to or the same as species volume module 42 (shown in FIG. 1 and described above).

Figure 3:
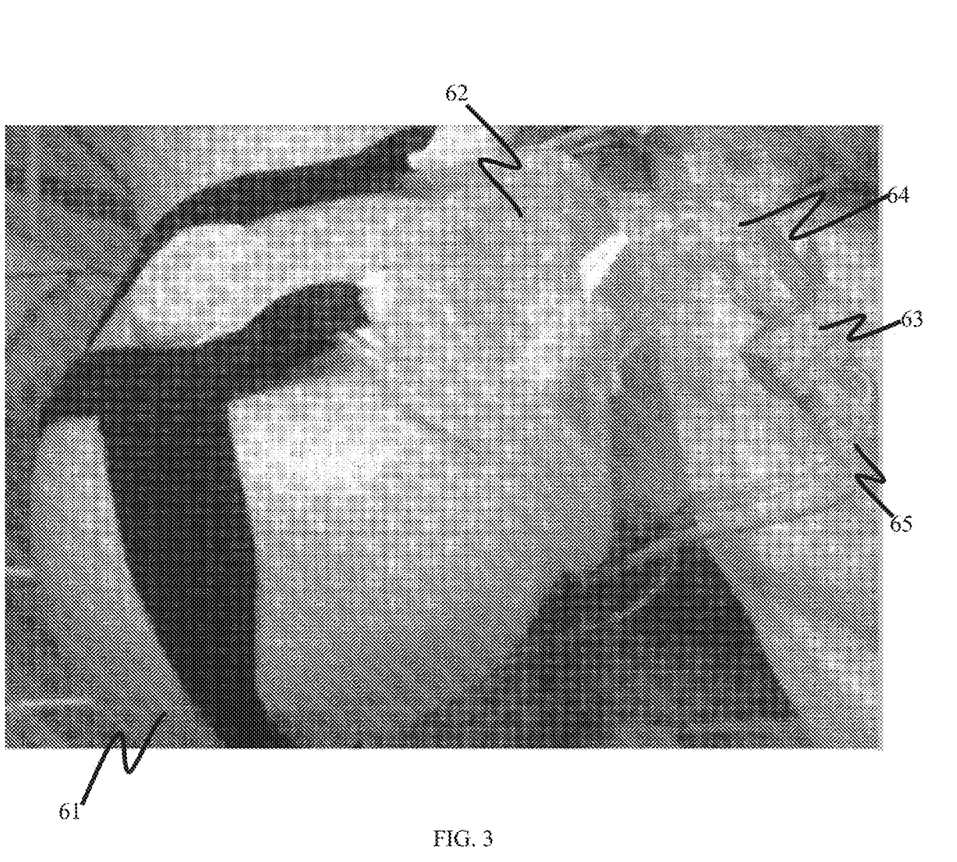
FIG. 3 illustrates a simulated patient interface used in an evaluation of non-invasive ventilation mask leak compensated VCO measurement according to an embodiment of the invention.

FIG. 3 illustrates a simulated patient interface used in an evaluation of non-invasive ventilation mask leak compensated $VCO_2$ measurement according to an embodiment of the invention. A styrofoam mannequin head 61 to which was glued a size large Performax mask (Philips Respironics, Murraysville, Pa.) 62 was used to simulate a patient interface. Flow through the mannequin mouth was directed to a test lung (TTL, Michigan Instruments, Grand Rapids, Mich.) using a 6.5 mm endotracheal tube. $CO_2$ gas was infused into the test lung using a precision mass flow controller (Alicat 1-SLPM-D, Alicat Scientific, Tucson Ariz.). The volumetric capnometry sensors (Flow/$CO_2$) 63 were connected between the vented elbow connector 64 and the exhalation port 65. The lung was ventilated using a V60 ventilator (Respironics/Philips, Carlsbad, Calif.) set at IPAP=18 and EPAP=4 cm $H_2O$. Respiratory rate was set at 10 Breaths per minute. Lung compliance was set at 50 ml/cm $H_2O$. The exhalation port was connected between the sensors and the hose.

$CO_2$ was infused into the test lung at 100, 150, 200, 250, 300, 350 and 400 ml/minute for 10 minutes at each infusion rate. Flow and $CO_2$ data was collected using the volumetric capnometer (NM3, Respironics/Philips, Wallingford, Conn.) interfaced to a PC. The exported waveforms were processed using a windows program written to implement the compensation algorithm. The resulting compensated $VCO_2$ measurement was compared against the actual $CO_2$ infusion rate.

The average measured inspired tidal volume was 2600 ml and the average measured expired tidal volume was 87 ml, or 96.7% of the inspired gas leaked out without being directly analyzed by the sensors.

The measured infused $CO_2$ rates were:

| Average Measured $VCO_2$ | $CO_2$ flow (ml/min) | Percent Error |
|---|---|---|
| 101.7 | 100 | 1.7% |
| 149.2 | 150 | −0.5% |
| 194.8 | 200 | −2.6% |
| 241.1 | 250 | −3.5% |
| 284.2 | 300 | −5.3% |
| 326.6 | 350 | −6.7% |
| 382.1 | 400 | −4.5% |

When the compensation for the effect of leaks and gas mixing is applied, the average error is only −3.1% with a reasonable standard deviation of 2.9%.

Details included herein are for the purpose of illustration based on what is currently considered to be the most practical and preferred embodiments; it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to determine a volume of carbon dioxide excreted by a subject during respiration, the system comprising:
one or more gas parameter sensors configured for placement at or near an airway of the subject and configured to generate first output sensor signals conveying information related to pressure and/or flow in a respiratory circuit;
a volumetric capnometer configured for placement at or near the airway of the subject and configured to generate second output sensor signals conveying information related to a concentration of carbon dioxide present in the respiratory circuit;
one or more physical computer processors configured by computer-readable instructions to:
determine the concentration of carbon dioxide in gas expired from the airway of the subject during expiration based on (i) the second output sensor signals and (ii) a volume of the respiratory circuit between the airway of the subject and the volumetric capnometer;
estimate gas leakage from the respiratory circuit during respiration based on the first output sensor signals; and
determine volumes of carbon dioxide excreted by the subject during individual breaths based on (i) the determined concentration of carbon dioxide and (ii) the estimated gas leakage from the respiratory circuit.

2. The system of claim 1, wherein the one or more processors are further configured to estimate gas leakage from the respiratory circuit as a function of pressure in the respiratory circuit based on the first output sensor signals.

3. The system of claim 1, wherein the one or more processors are further configured such that determination of the carbon dioxide concentration in gas expired from the airway of the subject comprises an adjustment to a measured concentration of carbon dioxide to account for a volume of the respiratory circuit between the airway of the subject and the volumetric capnometer.

4. The system of claim 1, wherein the one or more processors are further configured to estimate carbon dioxide volume leaked during expiration based on (i) the determined concentration of carbon dioxide and (ii) the estimated gas leakage from the respiratory circuit.

5. The system of claim 1, wherein the one or more processors are further configured to estimate carbon dioxide volume leaked during inspiration based on (i) the determined concentration of carbon dioxide and (ii) the estimated gas leakage from the respiratory circuit by the one or more processors.

6. The system of claim 1, wherein the one or more processors are configured such that the concentration of carbon dioxide in gas expired from the airway of the subject during expiration is correlated with the concentration of carbon dioxide present in the respiratory circuit by a correlation coefficient of $1-e^{-[Vexp/Vcircuit]}$, wherein $V_{exp}$ corresponds to a volume of gas expired by the subject determined via the one or more gas parameter sensors, and wherein $V_{circuit}$ corresponds to the volume of the respiratory circuit between the airway of the subject and the volumetric capnometer.

7. A method of determining a volume of carbon dioxide excreted by a subject during respiration, the method comprising:
   generating, by one or more first sensors at or near an airway of the subject, first output signals conveying information related to pressure and/or flow in a respiratory circuit;
   generating, by a volumetric capnometer at or near the airway of the subject, second output signals conveying information related to a concentration of carbon dioxide present in the respiratory circuit;
   determining, by one or more physical computer processors, the concentration of carbon dioxide in gas expired from the airway of the subject during expiration based on the second output sensor signals and a volume of the respiratory circuit between the airway of the subject and the volumetric capnometer;
   estimating, by the one or more processors, gas leakage from the respiratory circuit during respiration based on the first output sensor signals; and
   determining, by the one or more processors, volumes of carbon dioxide excreted by the subject during individual breaths based on (i) the determined concentration of carbon dioxide in gas expired from the airway of the subject and (ii) the estimated gas leakage from the respiratory circuit.

8. The method of claim 7, wherein estimates of gas leakage are determined as a function of pressure in the respiratory circuit based on the first output sensor signals.

9. The method of claim 7, wherein determination of the carbon dioxide concentration in gas expired from the airway of the subject comprises an adjustment to a measured concentration of carbon dioxide to account for a volume of the respiratory circuit between the airway of the subject and the volumetric capnometer.

10. The method of claim 7, further comprising estimating carbon dioxide volume leaked during expiration based on (i) the determined concentration of carbon dioxide in gas expired from the airway of the subject and (ii) the estimated gas leakage from the respiratory circuit.

11. The method of claim 7, further comprising estimating carbon dioxide volume leaked during inspiration based on (i) the determined concentration of carbon dioxide in gas expired from the airway of the subject and (ii) the estimated gas leakage from the respiratory circuit.

12. The method of claim 7, wherein the concentration of carbon dioxide in gas expired from the airway of the subject during expiration is correlated with the concentration of carbon dioxide present in the respiratory circuit by a correlation coefficient of $1-e^{-[Vexp/Vcircuit]}$, wherein $V_{exp}$ corresponds to a volume of gas expired by the subject determined via the one or more first sensors, and wherein $V_{circuit}$ corresponds to the volume of the respiratory circuit between the airway of the subject and the volumetric capnometer.

13. A system for determining a volume of carbon dioxide excreted by a subject during respiration, the system comprising:
   means for generating first output sensor signals conveying information related to pressure and/or flow in a respiratory circuit, the means for generating the first output signals configured for placement at or near an airway of the subject;
   means for generating second output sensor signals conveying information related to a concentration of carbon dioxide present in the respiratory circuit, the means for generating second output sensor signals configured for placement at or near the airway of the subject;
   means for determining the concentration of carbon dioxide in gas expired from the airway of the subject during expiration based on the second output sensor signals and a volume of the respiratory circuit between the airway of the subject and the means for generating second output sensor signals;
   means for estimating gas leakage from the respiratory circuit during respiration based on the first output sensor signals; and
   means for determining volumes of carbon dioxide excreted by the subject during individual breaths based on (i) the determined concentration of carbon dioxide in gas expired from the airway of the subject and (ii) the estimated gas leakage from the respiratory circuit.

14. The system of claim 13, wherein estimates of gas leakage are determined as a function of pressure in the respiratory circuit based on the first output sensor signals.

15. The system of claim 13, wherein determination of the carbon dioxide concentration in gas expired from the airway of the subject comprises an adjustment to a measured concentration of carbon dioxide to account for a volume of the respiratory circuit between the airway of the subject and the means for generating the second output signals.

16. The system of claim 13, further comprising means for estimating carbon dioxide volume leaked during expiration based on (i) the determined concentration of carbon dioxide in gas expired from the airway of the subject and (ii) the estimated gas leakage from the respiratory circuit.

17. The system of claim 13, further comprising means for estimating carbon dioxide volume leaked during inspiration based on (i) the determined concentration of carbon dioxide in gas expired from the airway of the subject and (ii) the estimated gas leakage from the respiratory circuit.

18. The system of claim 13, wherein the concentration of carbon dioxide in gas expired from the airway of the subject during expiration is correlated with the concentration of carbon dioxide present in the respiratory circuit by a correlation coefficient of $1-e^{-[Vexp/Vcircuit]}$, wherein $V_{exp}$ corresponds to a volume of gas expired by the subject determined via the means for generating first output sensor signals, and wherein $V_{circuit}$ corresponds to the volume of the respiratory circuit between the airway of the subject and the means for generating second output sensor signals.

* * * * *